US007805982B2

(12) United States Patent
Hilab

(10) Patent No.: US 7,805,982 B2
(45) Date of Patent: Oct. 5, 2010

(54) PORTABLE CORE FLOOD APPARATUS FOR CONDUCTING ON-SITE PERMEABILITY MEASUREMENTS

(75) Inventor: Victor V. Hilab, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 238 days.

(21) Appl. No.: 11/714,453

(22) Filed: Mar. 6, 2007

(65) Prior Publication Data
US 2008/0216559 A1  Sep. 11, 2008

(51) Int. Cl.
*G01N 15/08* (2006.01)
(52) U.S. Cl. .......................................................... 73/38
(58) Field of Classification Search ...................... 73/38
See application file for complete search history.

(56) References Cited

U.S. PATENT DOCUMENTS

| | | | |
|---|---|---|---|
| 3,839,899 A | | 10/1974 | McMillen |
| 4,543,821 A | * | 10/1985 | Davis, Jr. .................. 73/152.07 |
| 4,586,376 A | * | 5/1986 | Outmans ................... 73/865.8 |
| 4,679,421 A | * | 7/1987 | Barree ........................... 73/38 |
| 4,868,751 A | | 9/1989 | Dogru et al. |
| 4,884,438 A | * | 12/1989 | Jones et al. ............... 73/152.11 |
| 5,133,207 A | | 7/1992 | Wilson et al. |
| 5,261,267 A | * | 11/1993 | Kamath et al. .................. 73/38 |
| 6,289,725 B1 | | 9/2001 | Hubbell et al. |

FOREIGN PATENT DOCUMENTS

GB     2161942      1/1986

OTHER PUBLICATIONS

Jasco International Co., Ltd, Jasco/Comparison Proven Spectroscopy and Chromatography Technology, 2006, Asia.
Coretest Systems Product Listing, MBPR-3 Pinch Type Backpressure Regulator, 2000-2002, USA.

* cited by examiner

*Primary Examiner*—Hezron Williams
*Assistant Examiner*—Nathaniel Kolb
(74) *Attorney, Agent, or Firm*—Bracewell & Giuliani LLP

(57) ABSTRACT

A portable apparatus and method provide on-site permeability measurements of a core sample extracted from a subterranean reservoir. The portable apparatus is easily and conveniently transported to well locations for use on-site, thereby allowing the core sample to be tested in actual reservoir conditions. The apparatus can simultaneously test incoming liquids and liquids passing through the core sample, and can measure data in the forward and reverse flow directions. The apparatus requires only a single pump to pressurize and inject the liquid into the core sample.

13 Claims, 9 Drawing Sheets

| 3.0% NaCl Solution in Berea Core | |
|---|---|
| Flow rate/Area | Permeability |
| 0.0901 | 75.37 |
| 0.1802 | 74.11 |
| 0.3604 | 72.6 |
| 0.721 | 69.85 |
| 0.3604 | 69.48 |
| 0.1802 | 69.12 |
| 0.0901 | 70.96 |
| 0.0901 | 70.59 |
| 0.1802 | 69.12 |
| 0.3604 | 68.59 |
| 0.721 | 66.33 |
| 0.3604 | 65.72 |
| 0.1802 | 65.24 |
| 0.0901 | 65.72 |

*FIG. 13*

| DATA | |
|---|---|
| BEREA Core Plug in 3.0% NaCl Solution | |
| Solution using New Portable System | |
| Flow rate (cc/min) | Differential Pressure (psi) |
| 1 | 1.77 |
| 2 | 3.6 |
| 4 | 7.35 |
| 8 | 15.28 |
| 4 | 7.35 |
| 2 | 3.84 |
| 1 | 1.88 |
| 1 | 1.89 |
| 2 | 3.86 |
| 4 | 7.78 |
| 8 | 16.09 |
| 4 | 8.12 |
| 2 | 4.09 |
| 1 | 2.03 |

*FIG. 14*

PORTABLE CORE FLOOD APPARATUS FOR CONDUCTING ON-SITE PERMEABILITY MEASUREMENTS

BACKGROUND OF THE INVENTION

1. Field of the Invention

The present invention relates to petrophysical reservoir characterization, and, in particular, to on-site permeability measurements obtained of core samples collected from formation rock adjacent well bores in subsurface reservoirs to determine formation areas of interest.

2. Description of the Related Art

In the petroleum extraction and production industry, ascertaining the subterranean characteristics of reservoirs is of vital economic importance. Characteristics such as formation rock permeability and porosity help to indicate subsurface areas of increased fluid movement. In order to locate these areas, the permeability and porosity of the reservoir rock must be determined. Permeability refers to the ability of the reservoir rock to transmit fluids through many large interconnected pore spaces. Porosity is a measure of the capacity of the reservoir rock which is able to store oil and gas, or in other words, the volume of the pore space in a porous medium.

In current reservoir analysis methods, so far as known, porosity and permeability measurements have been determined by removing core samples from a well drilled into a reservoir rock formation of interest. So far as known, once these samples had been removed, they were transported to a testing facility which was at a laboratory and not at the site of the well. Once the samples were transported to the laboratory, the technician or scientist could begin conducting various tests to determine the permeability of the reservoir samples.

There were many disadvantages to this type of reservoir analysis. First, preserving the fresh and original state of the core sample is highly important in ascertaining various data, such as water quality, biocide functioning, and microbial activity. However, during transportation to the experiment lab, maintaining the original state was very difficult. Also, the test fluids used in the lab tests might differ to an appreciable extent from the actual fluids at the reservoir or to be used at the reservoir. Further, in current analysis methods, the time it took to transport the samples to the laboratory resulted in lost time and higher production costs. Drilling companies spend vast amounts of money each day performing drilling operations; therefore, any way to reduce this time would be advantageous. Additionally, the present testing systems, so far as is known, are too large and cumbersome to be efficiently transported on-site to conduct testing.

SUMMARY

Briefly, the present invention provides a new and improved apparatus for permeability measurements of a core sample obtained from a subterranean reservoir. The apparatus of the present invention includes a core sample holder receiving a core sample obtained from the subterranean reservoir for permeability testing. The core sample holder has a test inlet port for receiving fluid for permeability testing of the core sample and also has an outlet port for exit of the fluid. An accumulator in the apparatus contains fluid for application to the core sample holder for permeability testing of the core sample, and a pump applies fluid from the accumulator to the core sample holder at selected controlled fluid pressure and flow rate. A pressure regulator is in fluid communication with the core sample holder to establish an inlet pressure for the fluid at the test inlet port of the core sample holder for the applied fluid. A pressure transducer section in the apparatus measures pressure differential of the fluid between the inlet and outlet ports of the core sample holder, and a data processor obtains a measure of the relative permeability of the core sample based on the pressure differential measurements and the fluid flow rates.

The present invention also provides a new and improved modular apparatus transportable to a well site for permeability measurements of a core sample obtained from a subterranean reservoir of the well. The modular apparatus includes a container module having a floor base, side walls and a partition between the side walls to form front and rear compartments. A core sample holder is mounted with the floor base of the module to receive a core sample obtained from the subterranean reservoir for permeability testing. The core sample holder has a test inlet port for receiving fluid for permeability testing of the core sample, and an outlet port for exit of the fluid. An accumulator is mounted with a side wall of the module and contains fluid for application to the core sample holder for permeability testing of the core sample. A pump is mounted with the floor of the module and applies fluid from the accumulator to the core sample holder at selected controlled fluid pressure and flow rate for sample testing. A pressure regulator in fluid communication with the core sample holder establishes an inlet pressure for the fluid at the test inlet port of the core sample holder. A pressure transducer section mounted with the partition of the module measures pressure differential of the fluid between the inlet and outlet ports of the core sample holder. A data processor mounted on an upper portion of the module for obtains measures of the relative permeability of core samples based on the pressure differential measurements and the fluid flow rates.

The present invention further provides a new and improved method of on-site permeability measurements of a core sample extracted from a subterranean reservoir adjacent a well. According to the method of the present invention, a modular test apparatus is transported to a well site for permeability measurements of a core sample obtained from a subterranean reservoir of the well. A core sample obtained from a subterranean reservoir is inserted into the core sample holder. A test fluid is pressurized and applied to the core sample holder at a test flow rate. Flow rate and pressure differential data measurements are acquired for the core sample being tested, and a measure of the relative permeability of the core sample at the well site is obtained based on the pressure differential measurements and the fluid flow rates.

BRIEF DESCRIPTION OF THE DRAWINGS

The objects, advantages and features of the invention will become more apparent by reference to the drawings appended thereto, wherein like numerals indicate like parts and wherein an illustrated embodiment of the invention is shown, of which:

FIGS. 13 and 14 are charts listing the data output of test results obtained according to the present invention.

DETAILED DESCRIPTION OF THE INVENTION

Figure 1:
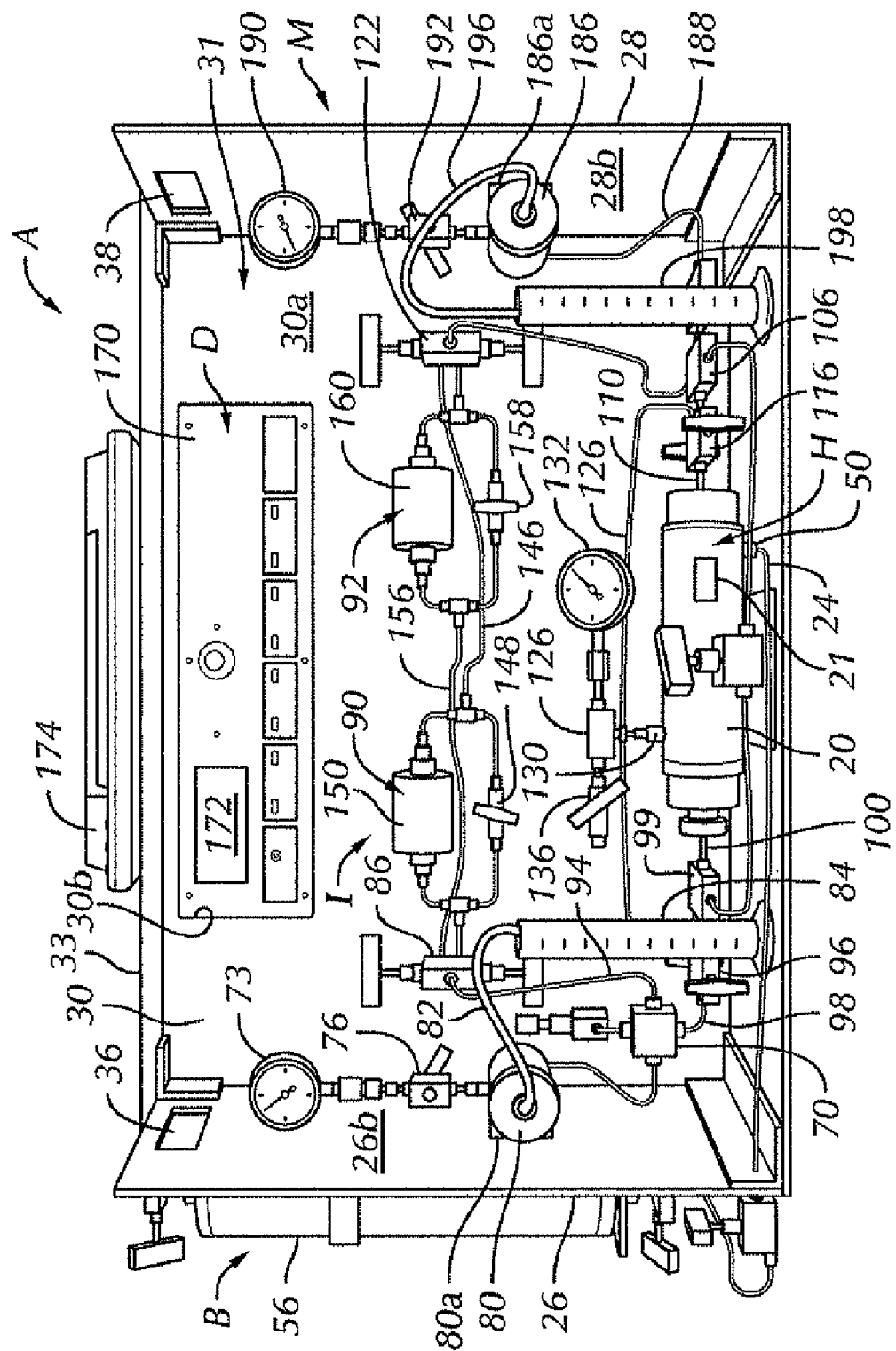
FIG. 1 is a front view of the portable testing apparatus according to an embodiment of the present invention.

In the drawings (FIGS. 1-5), a portable, on-site core permeability testing apparatus A is shown according to the present invention. The permeability testing apparatus A of the present invention is modular and compact, as will be set forth, and thus is easily transportable, even to remote well sites. The permeability testing apparatus A accordingly measures fluid permeabilities, such as water or oil, on-site of reservoir samples at ambient pressure or at reservoir pressure conditions. The on-site permeability testing apparatus A enables scientists and technicians to determine the impact of injected brine or produced oil on reservoir core permeability in a minimal amount of time. Since data are obtained from freshly collected formation core samples, the quality of actual well injection water or brine can be assessed, and accurate measurements of biocide functioning and microbial activity in the reservoir are made available. Each of these advantages is significant. Further, since the apparatus A is capable of use at the well site with freshly collected formation samples, the results are more accurate than those obtained in an off-site lab due to changes in the field water quality during transport times.

The on-site permeability testing apparatus A includes a core holder section H, which includes a core sample container 20 which contains the formation core sample extracted from a subterranean reservoir. As will be set forth, the core sample container 20 is pressurized in the apparatus A during testing to desired pressures of either brine or oil at selected flow rates for permeability testing purposes. If desired, a heating tape 21 can be applied to core sample container 20 in order to heat the core sample to a desired ambient or reservoir temperature. During testing, fluids, such as water or oil, are pressurized and pumped across the core sample in core sample container 20 by a pump P.

The testing apparatus A includes the pump P (FIGS. 4 and 5) which is capable of providing calibrated fluid pressure and volume for core sample permeability testing. The pump P is preferably of the type known as a high pressure liquid chromatography or HPLC pump of a suitable commercially available type. A suitable pump, for example, is a Model PU-2086 HPLC pump available from Jasco International Co., Ltd., of Tokyo, Japan. The pump P is connected to an accumulator bank B which can selectively furnish either water/brine or oil to the core holder H. With the present invention, the apparatus A is easily transportable to and usable at well locations on-site, even remote ones. Thus, the fluids used in testing a formation core sample can be those encountered in the same well from which the core sample was obtained.

Measurement instrumentation I in the form of a first or low differential pressure transducer section T and a second or high pressure differential transducer section S is connected to obtain pressure measurements in a manner to be set forth for permeability testing and measurement purposes. A data acquisition section D is connected to the measurement instrumentation I (FIG. 5) for processing, recording, storage and display of data measurements obtained from tests performed on core samples in the core holder if The testing apparatus A also includes a filter, to be described further below, which is used to filter solids and other sediments from the testing fluids, thereby preventing clogging of the lines.

Figure 4:
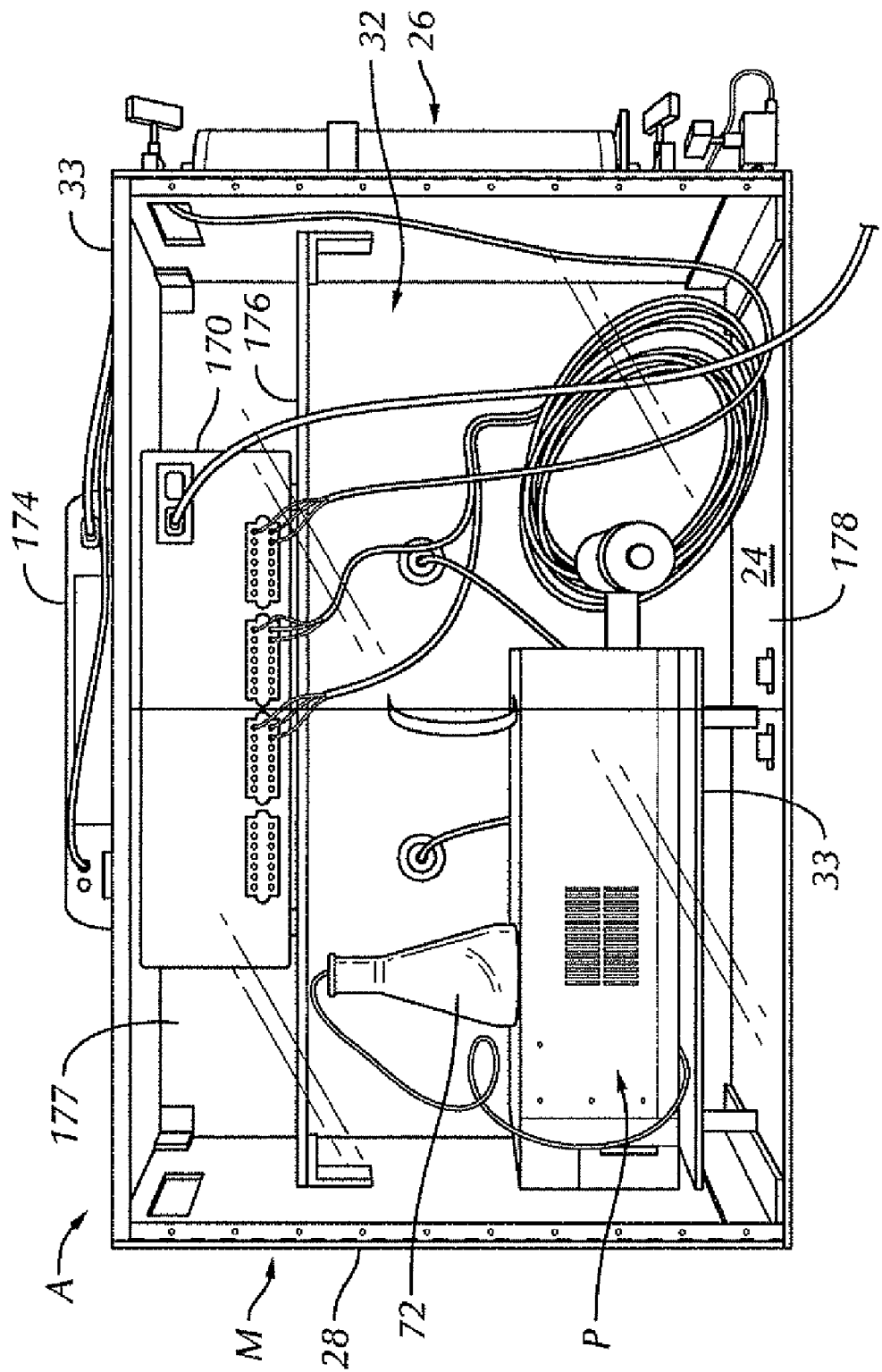
FIG. 4 is a rear view of the portable testing apparatus of FIG. 1.
Figure 5:
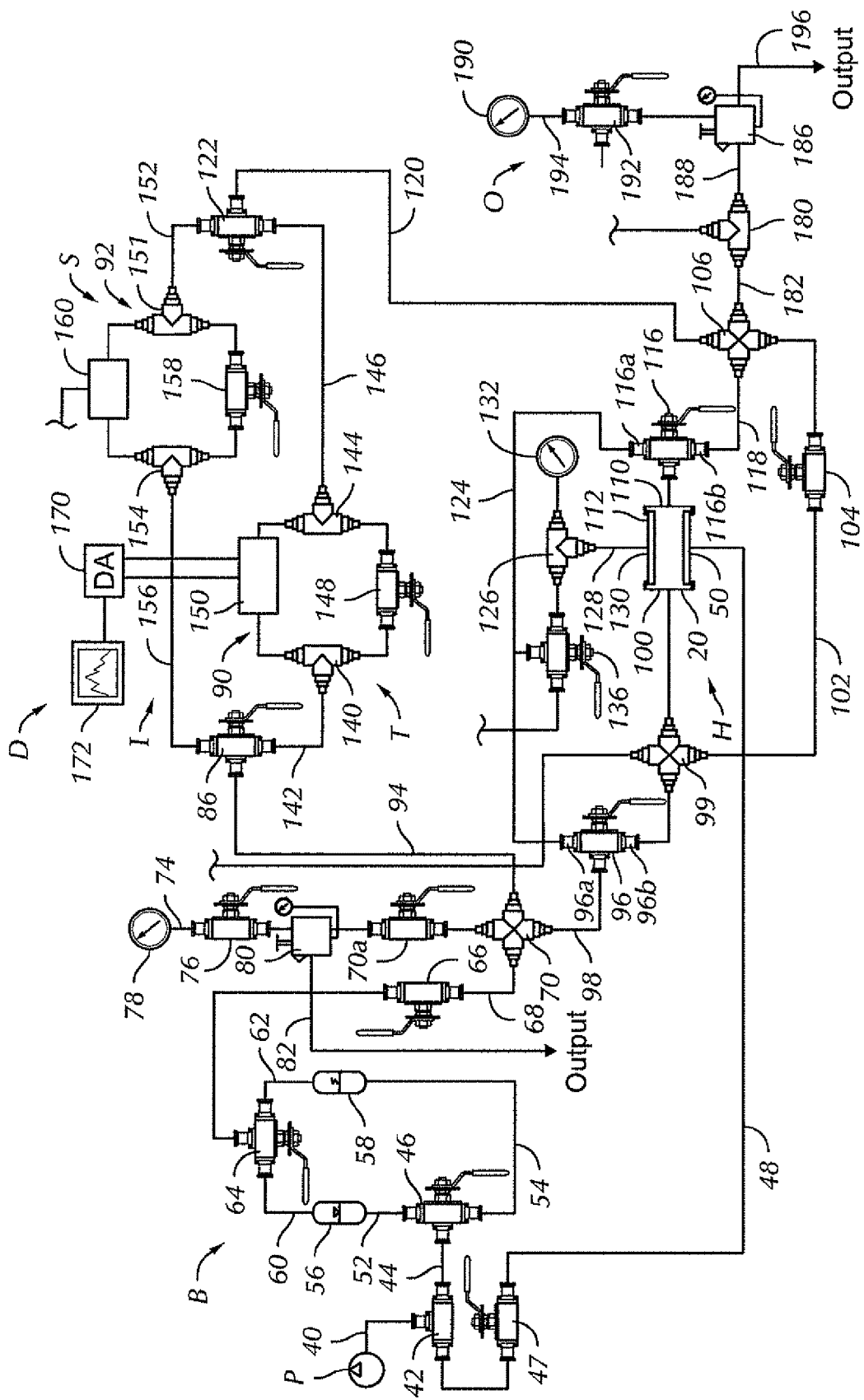
FIG. 5 is a schematic diagram of the interconnection and valving arrangement of the components of the portable testing apparatus of FIG. 1.

The apparatus A is mounted in a container module M (FIGS. 1-4) which is modularized for ease of transport to remote well sites. The container module is easily lifted and moved by two people onto a vehicle for transport to a well site. The container module M has a base or floor 24, two upright side walls 26 and 28, and a central partition or wall 30 which separates the module M into a front compartment 31 (FIG. 1) and a rear compartment 32 (FIG. 4). An upper ledge or wall 33 is mounted above the walls 26, 28 and 30.

As will be set forth, the fluid permeability testing components, valving and interconnection fluid tubing and pipes of the apparatus A are mounted in the module M for ease of transport and storage. Typical dimensions of the container module M are twenty-four inches high, twenty-five inches deep and thirty inches wide. The side walls 26 and 28 both have one or more hand grip portals or slots formed therein as indicated at 36 and 38, respectively, for ease of lifting and loading the apparatus A into a vehicle for transport.

The pump P is connected through a fluid tube or pipe 40 to a three way connector 42 which is in turn connected through a fluid tube 44 and a two stem, three way control valve 46 to the fluid accumulator bank B. The pump P is also connected by a check or bypass control valve 47 and a fluid tube or pipe 48 to a centrally located inlet port 50 of the core sample container 20.

Figure 2:
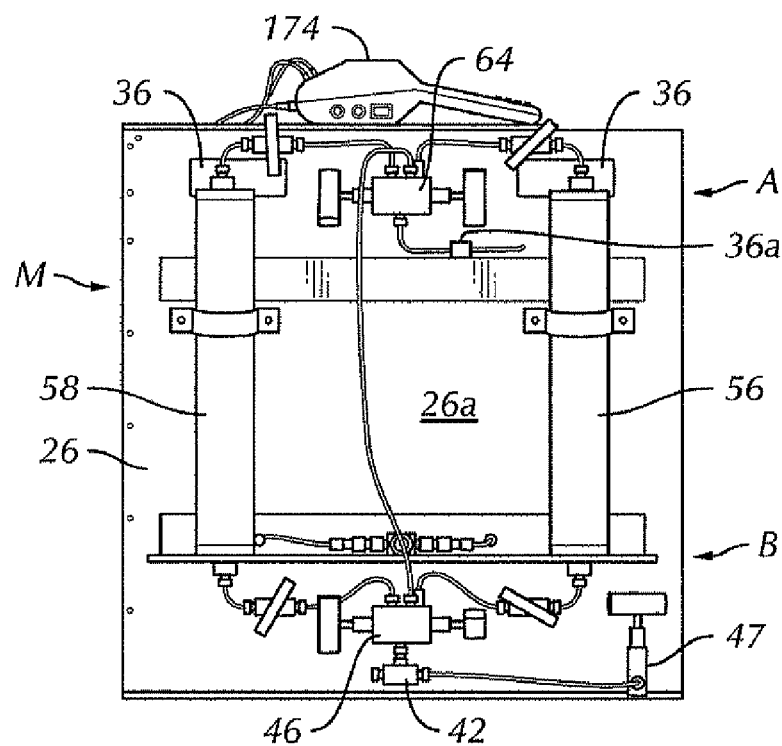
FIG. 2 is a left side view of the portable testing apparatus of FIG. 1.
Figure 3:
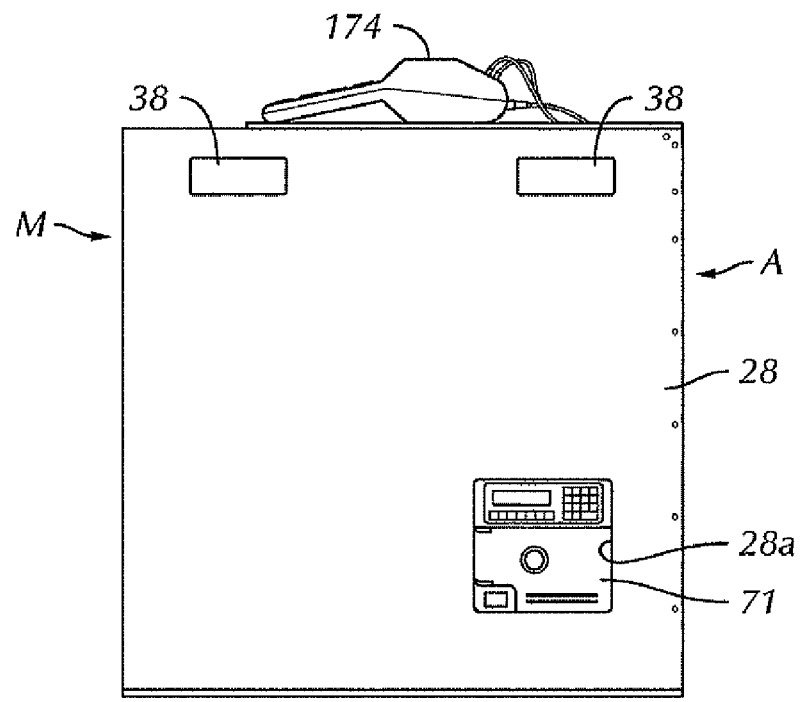
FIG. 3 is a right side view of the portable testing apparatus of FIG. 1.

The control valve 46 is connected by fluid tubes 52 and 54, respectively, to a brine accumulator 56 and an oil accumulator 58 of the accumulator bank B. Each of the accumulators 56 and 58 is preferably of the floating piston type and stores a volume of fluid under regulated and controlled pressures and flow rates for the purpose of permeability testing of core sample specimens with the apparatus, as will be described. The filter may be located within the accumulator 56, or at an outlet port of the accumulator 56, or as shown at 36a in the line to valve 46 (FIG. 2).

The accumulators 56 and 58 are each connected as indicated at fluid tubes 60 and 62 to a two stem, three way control valve 64 at the outlet of the accumulator bank B. The three way control valve 64 in a first of its three positions blocks flow of fluid from the accumulator bank B, and in its second and third positions allows either the brine in accumulator 56 or the oil in oil accumulator 58, as the case may be, to pass from the accumulator bank B to a control valve 66. The control valve 66 is connected by a fluid tube 68 to a four way connector manifold 70. Control valve 66 when opened allows fluid flow from the accumulator bank B to the core sample container 20 for testing purposes.

The valves 42, 46, 64 and 66, the brine accumulator 56, the oil accumulator 58 and their associated connection fluid tubes or piping are mounted on an outer surface 26a (FIG. 2) of the side wall 26 of the module M. The pump P is located in the rear compartment 32 (FIG. 4) on a stand or platform as shown at 33 on the floor 24 of the module M behind the central wall or partition 30 for the purposes of weight distribution. The fluid tube 40 which connects the pump P to the valve 42 extends through the side wall 26 of the module M to the connector 42. The core sample container 20 is mounted on the floor 24 of the module M.

The pump P is provided with a control or instrumentation panel 71 (FIG. 3) which is accessible through an opening 28a (FIG. 4) formed in the side wall 28 of the module M. One or more fluid containers 72 of test fluids such as brine or oil are, as shown in FIG. 4, located in the rear compartment 32 such as by being mounted on the pump P. Fluids in the containers 72 are furnished to the pump P and provided therefrom as test fluids for permeability testing in the apparatus A.

A pressure gauge 73 is connected through a fluid tube 74 to the four way manifold 70 through a control valve 76 to an inlet pressure regulator 80. The pressure regulator 80 is connected to the manifold 70 by a control valve 70a. Pressure regulator 80 controls the inlet pressure to the core sample holder section H according to the desired test conditions. The pressure regulator 80 is connected to a fluid outlet and vent tube 82 to convey excess outlet brine or oil to a suitable waste or recycling vessel or container 84 located on the floor 24 of the module M. Container 84 can be marked or otherwise calibrated to indicate its volumetric contents. The pressure gauge 73 is connected to the inlet pressure regulator 80 when the control valve 76 is open so that pressure at the inlet to the sample holder section H may be observed by operators of the apparatus A.

The pressure regulator 80 is capable of obtaining samples of the fluid while maintaining pore pressure on the core sample holder section H. Although severable types of such pressure regulators may be used, in a preferred embodiment a suitable example pressure regulator may be a Model MBPR-3 back pressure regulator available from Coretest Systems, Inc. of Morgan Hills, Calif. The apparatus A can thus sample any fluid used in the inlet or the outlet without disturbing permeability testing measurements and without removing or reducing pore pressure.

The pressure regulator 80 is mounted as indicated by a bracket or comparable structure 80a on inside surface 26b (FIG. 1) of the side wall 26 of module M. The pressure gauge 73 is mounted in a comparable manner to the same inside surface 26b.

A two stem, three way control valve 86 connected at the inlet of each of a low pressure differential transducer section 90 and a high pressure differential transducer section 92 of the measurement instrumentation I receives fluid through a tube 94 from the four way manifold 70. Control valve 86 in a first of its three positions blocks flow of fluid from manifold 70, and in its second and third positions allows fluid to pass to the low pressure differential transducer section 90 and the high pressure differential transducer section 92 of the measurement instrumentation I, as the case may be, for obtaining pressure data readings in the data acquisition section D regarding fluids in the accumulator bank B. The components of the transducer sections 90 and 92 are mounted on a front surface 30a (FIG. 1) of the central wall 30 of the module M.

A two stem, three way control valve 96 in the sample holder section H of the apparatus A is connected to the manifold 70 by a fluid tube 98. The valve 96 controls application of test fluids from the accumulator bank B through a manifold 99 to a test fluid inlet port 100 of the core sample container 20. The manifold 70 is also connected to the instrumentation section I by the fluid tube 94, where either the low differential pressure transducer 90 or the high pressure differential transducer 92 may be selectively connected to sense pressure conditions. Pressure conditions at inlet port 100 of the core sample container 22 are sensed and converted in the transducers of instrumentation section I into electrical signals and transferred to the data acquisition section D. The electrical connections for transferring the signals for this purpose are not shown in the drawings so that other structure may be more clearly seen.

With the present invention, the differential pressure transducer sets include preferably at least two differential transducers 90 and 92 which can be selectively used to sense pressure differentials in different pressure sensing ratings or ranges. This is done so that flexibility is provided to measure low and high core permeabilities. For example, for core samples with expected very high permeability, differential pressure transducer section 90 with a relatively low range may be used to obtain more accurate results. Conversely, for core samples with expected low permeability, differential pressure transducer section 92 with a relatively high pressure differential range may be used.

The manifold 99 is also connected through a fluid tube 102 and a control valve 104 to a second four way distribution manifold 106 for application of reverse flow and pressure conditions to a test inlet port 110 at an end portion 112 of the core sample container 20. A two stem, three way control valve 116 is connected through a fluid tube 118 to the manifold 106. The control valve 116 allows application of fluid from the accumulator bank B to the core sample container 20 at test inlet port 110 as testing procedures require.

The manifold 106 is also connected by a fluid tube 120 to a two stem, three way control valve 122 at an inlet side of the high pressure differential transducer section 92 of the measurement instrumentation I. The control valve 116 is also connected by a fluid tube 124 to control valve 96 for fluid routing purposes as testing procedures require. Manifold 106 additionally is connected to an outlet or fluid outlet section O of the apparatus A, as will be described.

A three way connector 126 is connected by a fluid tube 128 to a central outlet port 130 in the core sample container 22. A pressure gauge 132 is in fluid communication through connector 126 with the central outlet port 130 so that pressure at the outlet of the core holder section H may be observed by operators of the apparatus A. A two stem, three way control valve 136 in fluid communication with the connector 126 and central outlet port 130 is connected (not shown) to the fluid pressure transducer sections 90 and 92. The gauge 132, transducer sections 90, 92 and valve 136 are mounted with the surface 30a of the central wall 30 of the module M.

The transducer sections 90 and 92 sense pressure conditions at the outlet port 130 of the core sample container 20 and convert these measurements into electrical signals for transfer via suitable electrical or signal connection to the data acquisition section D. Electrical power for the components of apparatus A needing such power is typically provided by suitable connections to the well site power, although generators, batteries or other power sources may be used, if desired.

The control valve 122 is connected to both the low pressure differential transducer section 90 and the high pressure differential transducer section 92 of the measurement instrumentation I. Control valve 122, in a comparable manner to valve 86, in a first of its three positions blocks flow of fluid from its associated manifold 106, and in its second and third positions allows fluid to pass to the low pressure differential transducer section 90 and the high pressure differential transducer section 92 of the measurement instrumentation I, as the case may be, for obtaining data readings in the data acquisition section D regarding fluids in the accumulator bank B. The control valves 86 and 136 are each operable independently of each other and are connected to provide the apparatus A with multichannel data acquisition capability. Differential pressures at different locations in the apparatus A can thus be sensed and recorded while tests are in progress, without need to affect the test operations then under way.

The low pressure differential transducer section 90 of measurement instrumentation I includes a three way fluid connector 140 connected to an outlet of the control valve 86 by fluid tube 142 and a three way fluid connector 144 connected to an outlet of the control valve 122 by fluid tube 146. A bypass control valve 148 and a low differential pressure transducer 150 are connected in alternate flow paths between the connectors 140 and 144. Depending on the setting of the bypass control valve 148, fluid pressure conditions in low ranges in the core sample holder 20 can be sensed by the low differential pressure transducer 150 and converted to electrical signals which are furnished to the data acquisition section D.

Similarly, the high pressure differential transducer section 92 of measurement instrumentation I includes a three way fluid connector 151 connected to an outlet of the control valve 122 by fluid tube 152 and a three fluid connector 154 connected to an outlet of the control valve 86 by a fluid tube 156. A bypass control valve 158 and a high differential pressure transducer 160 are connected in alternate flow paths between the connectors 151 and 154. Depending on setting of the bypass control valve 158, fluid pressure conditions in high ranges in the sample holder chamber 20 can be sensed by the differential pressure transducer 160 and converted to electrical signals which are furnished by suitable communication to the data acquisition section D.

The data acquisition unit D includes a data acquisition processor/computer 170 of any suitable commercially available type. The measurements obtained by the pressure transducers described above in the apparatus A are received by the data acquisition computer 170 for processing, storing and storage according to the present invention in order to determine permeability of the core sample currently being tested in the core sample chamber or container 20.

The computer 170 can be a portable or PC compatible computer of any conventional type of suitable processing capacity such as those available from any of several sources. The computer 170 may be a laptop computer, notebook computer or any other suitable data processing apparatus. It should also be understood that other types of digital signal processors or other forms of data processors may also be used, as well.

In any case, the processor of the computer 170 accesses the data measurements provided from the measurement instrumentation I through a data input/output unit 172 to undertake the pressure reading signal processing and analysis logic of the present invention, which may be executed by a processor as a series of computer-executable instructions in the computer 170. The processed results from computer 170 are then available for analysis on an output display or printer of suitable display or plotter of the data input/output unit 172. The data input/output unit 172 also includes an input and control portion 174 such as a keyboard, touchpad, mouse or other suitable data and instruction entry mechanism.

The computer 170 is mounted on a shelf 176 located in the rear compartment 32 (FIG. 4) adjacent an opening 30*b* (FIG. 1) formed at an upper central portion of the partition or wall 30 below the upper ledge or wall 33. The data input/output unit 174 is preferably mounted on the upper ledge or shelf 33. The rear compartment 32 of the module M is preferably enclosed, having doors 177 and 178 which may be opened for access to the computer 170, the pump P and the fluid containers 72. Locks may be provided for the doors 177 and 178, if desired, for security or safety purposes.

In the fluid outlet section O (FIG. 5) of the apparatus A, a three-way or T connector 180 is connected to the manifold 106 by a fluid tube 182. The connector 180 is connected to the instrumentation section I, which senses outlet fluid pressure conditions of the core sample holder section H in the manner set forth above, converting the sensed pressure conditions into electrical signals. The signals from the pressure differential transducers 150 or 160, as the case may be, are furnished to computer 170 in the data processing section D for processing.

An outlet fluid pressure regulator 186 is in fluid communication with the connector 180 through fluid tube 188 and serves to establish the required outlet pressure in the required testing outlet pressure in the core sample holder section H for the various tests and data measurements. A pressure gauge 190 is connected by a control valve 192 through fluid tube 194 so that pressure at the outlet of core sample holder section H may be observed by the operator or technician. An outlet drain tube 196 connects the pressure regulator 186 to a fluid drainage or disposal container 198 at the outlet of the apparatus A. The container 198 is located on the floor 30 of the module M and is calibrated or otherwise marked or indexed to provide indications of its volumetric content.

As was the case with pressure regulator 80 at the inlet, the pressure regulator 186 is capable of obtaining samples of the fluid while maintaining pore pressure on the core sample holder section H. Although severable types of such pressure regulators may be used, in a preferred embodiment a suitable example pressure regulator may be a Model MBPR-3 of the type available from Coretest Systems, Inc. of the type used as pressure regulator 80. The apparatus A can thus sample any fluid used in the inlet or the outlet without disturbing permeability testing measurements and without removing or reducing pore pressure.

The pressure regulator 186 is mounted as indicated by a bracket or comparable structure 186*a* on inside surface 28*b* (FIG. 1) of the side wall 28 of module M. The pressure gauge 190 is mounted in a comparable manner to the same inside surface 28*b*.

Figure 6:
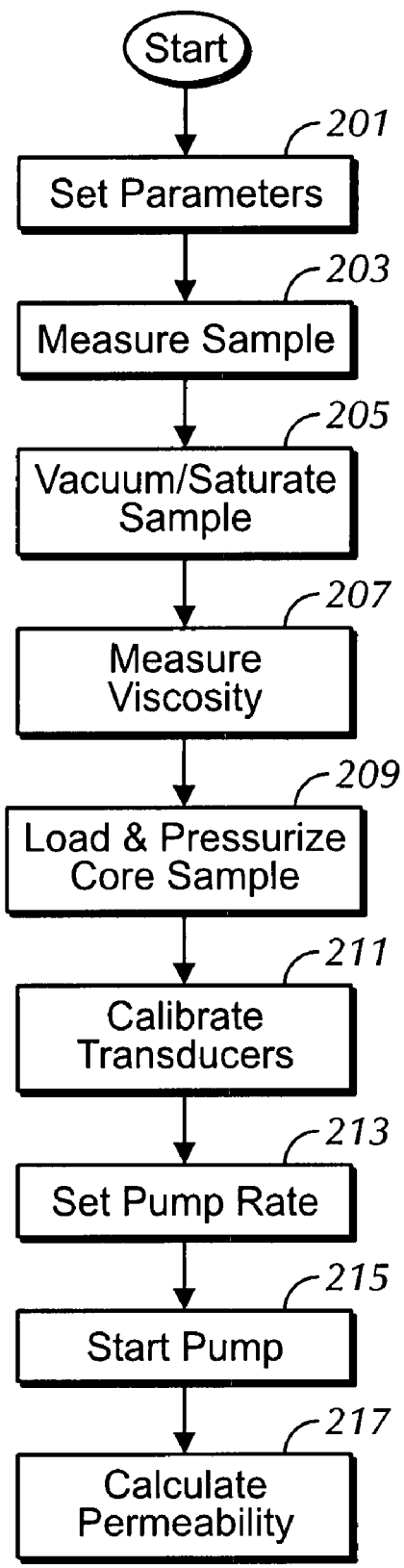
FIG. 6 is a flow chart illustrating a method sequence of steps according to the present invention.

Permeability testing according to the present invention is performed in the manner indicated schematically in the process flow chart of FIG. 6. With the apparatus A on-site, an operator or technician sets or establishes the desired testing parameters at step 201. For example, these parameters can include setting the overburden pressure, pore pressure, and the flow rate of the fluids. Once the parameters have been set, the technician then measures the diameter and length of the sample in step 203. In the preferred embodiment, core sample holder 20 can accommodate a 3 inch long core sample with a diameter of 1.5 inches. However, those skilled in the art realize the core holder can be designed to accommodate other sizes.

At step 205, the technician vacuums and saturates the sample with a brine or NaCl solution. At step 207, the technician then measures the viscosity of the brine solution at room temperature. Once viscosity measuring is complete, the technician then loads the sample into core holder 20. Pump P is then used to pressurize to simulate the formation overburden with distilled water up to a suitable pressure, such as 1500 psi, as indicated at step 209. At step 211, the technician then calibrates inlet pressure transducer 102, inlet pressure regulator 80, as well as outlet pressure transducer 184 and pressure regulator 186. Thereafter, the technician fills piston accumulator 56 with filtered brine solution, preferably that used in the well from which the core sample was obtained. The operator then connects all system lines, and sets the valves of the apparatus A in a forward flow direction of the fluid from the accumulator bank B into the port 100 of the core sample holder 20.

At step 213, the technician sets the pump rate of the pump P to a first desired flow rate. At step 215, the technician starts the pump P and opens the by-pass valve 47 to the core holder 20 in order to flush the fluid tubes or lines. After the fluid lines are clear, the technician then checks to be certain the pressure differential or dP readings are zero. Once checked, the by-pass valve 47 is then closed, and differential transducers in instrumentation section I begin to monitor the differential pressure across core sample holder 20 until a stabilized pressure drop at the desired rate is achieved.

The fluid permeability of the sample in the core sample holder 20 then proceeds over the specified range of pressures and flow rates. The testing procedure can be performed for a number of desired flow rates and pressure differentials. The data acquisition section D receiving data measurements for the desired flow rates and pressure differentials and computes, stores and displays the permeability testing results. For forward flow, valve 96 is set so that flow is permitted at 96b and blocked at 96a, while valve 116 is set so that flow is permitted at 116b and blocked at 116a. For reverse flow, valve 96 is set to opposite flow conditions, permitting flow at 96a and blocking flow at 96b. Similarly, valve 116 is set for reverse flow so that flow is permitted at 116a and blocked at 116b.

The relative permeability of a core sample is determined in the data acquisition system computer 170, typically using Darcy's Law of Relative Permeability. Code for the computer 170 is conventional and can be using any well known programming language, such as C, C++, or Java. Darcy's Law is a known relation used in permeability testing, expressed as a derived equation that describes the flow of a fluid through a porous medium. The relation of the permeability coefficient for a formation core sample of a particular volume based on fluid flow therethrough may be expressed as:

$$K = \frac{245 \cdot dV \cdot U \cdot L}{dT \cdot A \cdot dP}$$

In the foregoing expression of Darcy's law:
K=permeability coefficient, measured in Darcy units
dV=throughput volume, in cc
U=viscosity, in centipoise or cP (liquid)
L=length of the sample (cm)
A=cross-sectional area of sample (diameter$^{2 \times 3.1416}$) (4)=area, cm$^2$,
dP=pressure differential in psi, and
dT=time.

After data acquisition system D has determined the permeability coefficient during a test of a sample for a particular throughput volume and pressure differential, the calculated data can be transferred to a workable file program, such as EXCEL, contained in memory associated with the computer 170, and plotted or displayed, or both, with input/output unit 172.

Figure 7:
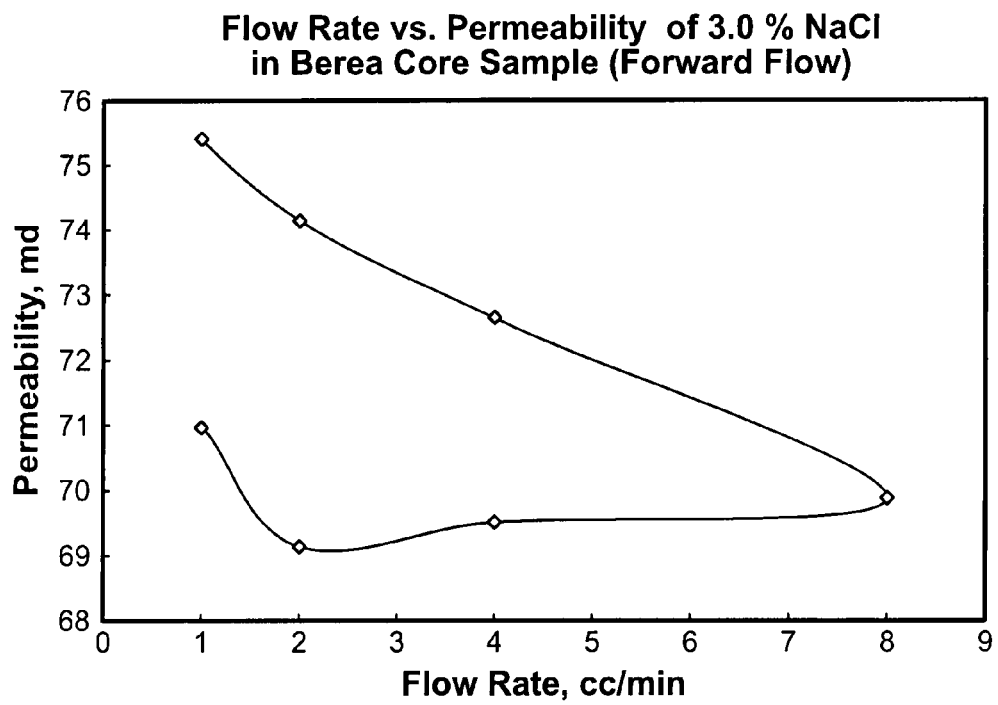
FIGS. 7, 8 and 9 are data displays illustrating example measurements of permeability as a function of flow rate obtained according to the present invention.
Figure 8:
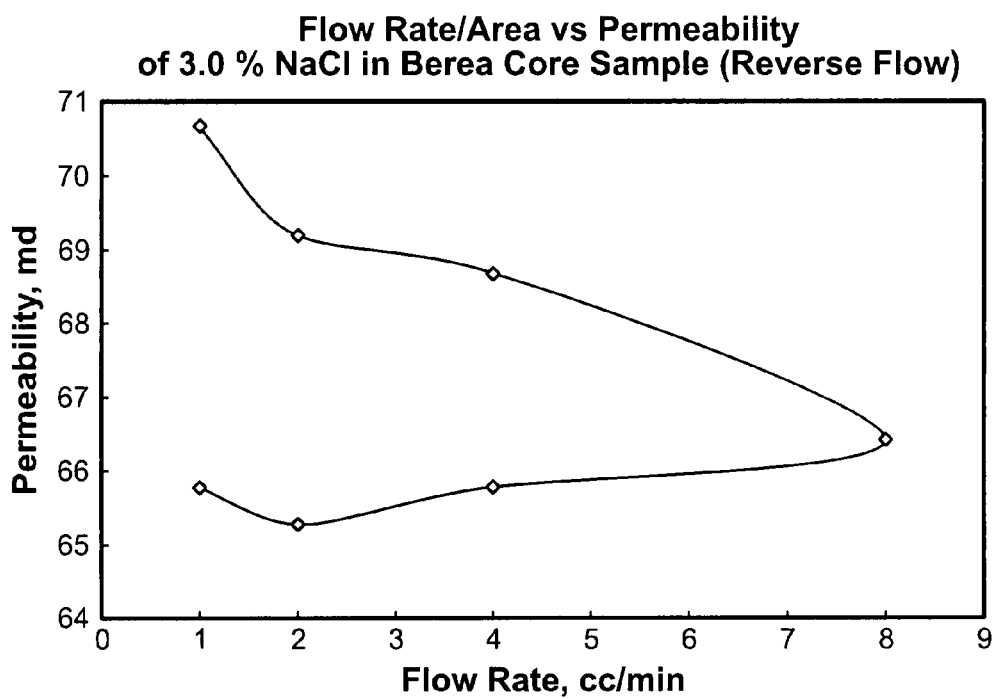
Figure 9:
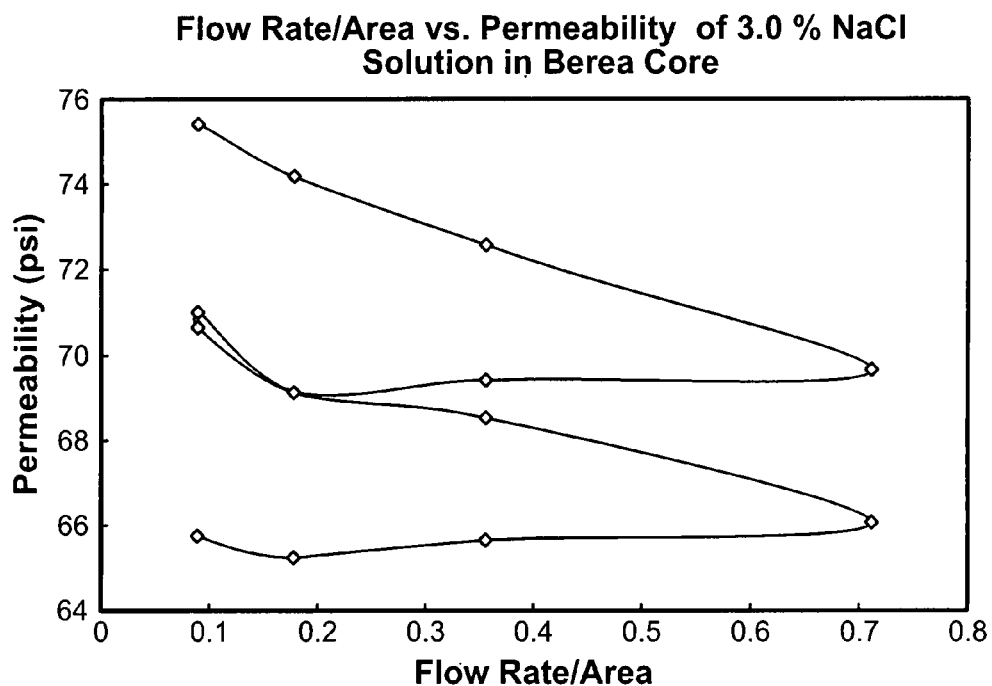

Examples of permeability testing according to the present invention are illustrated in FIGS. 7 through 14. Conventional sandstone sample plugs of the known Berea core type with a 3% brine or NaCl solution were used, and FIG. 13 is a replicated chart of example data readings for permeability coefficients obtained over a range of flow rates per unit area with an apparatus according to the present invention. FIG. 7 is a plot of those portions of the data from FIG. 13 for forward flow of the solution through the sample, and FIG. 8 is a plot of those portions of the data from FIG. 13 for reverse flow of the solution through the sample. FIG. 9 is a composite plot of the data displayed in FIGS. 7 and 8. The results are used to compare the results between forward and reverse flow rates. Data from reverse flow allows a determination of whether damage to a core sample from pressure and fluid passage has occurred. If the damage is only on the face of the inlet side of the core sample, and not internal, the pressure differential readings do not differ to any appreciable extent. Based on the pressure differential data from both the forward and reverse flow rates, damage to the formation indicated by the sample can be assessed.

Figure 10:
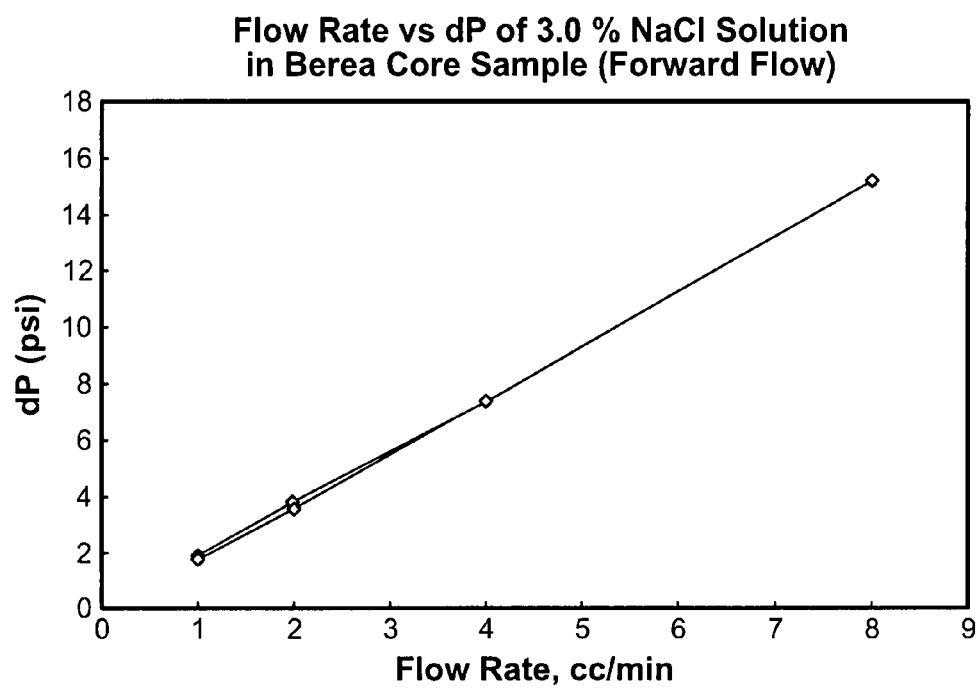
FIGS. 10, 11 and 12 are data displays illustrating example measurements of differential pressure as a function of flow rate obtained according to the present invention.
Figure 11:
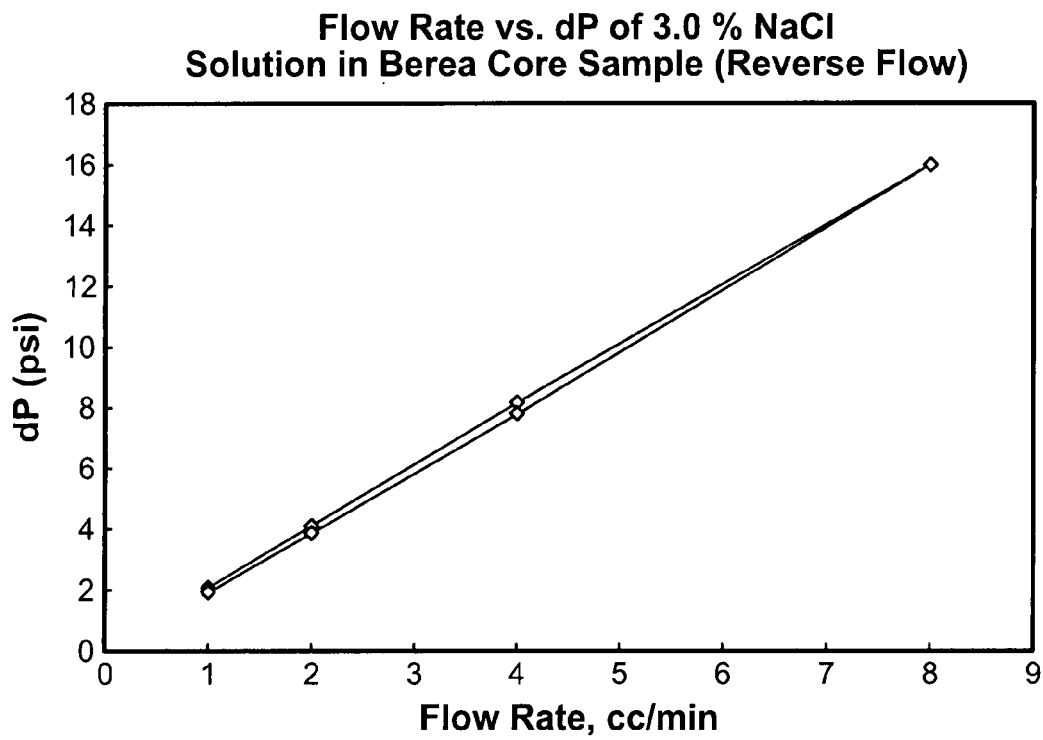
Figure 12:
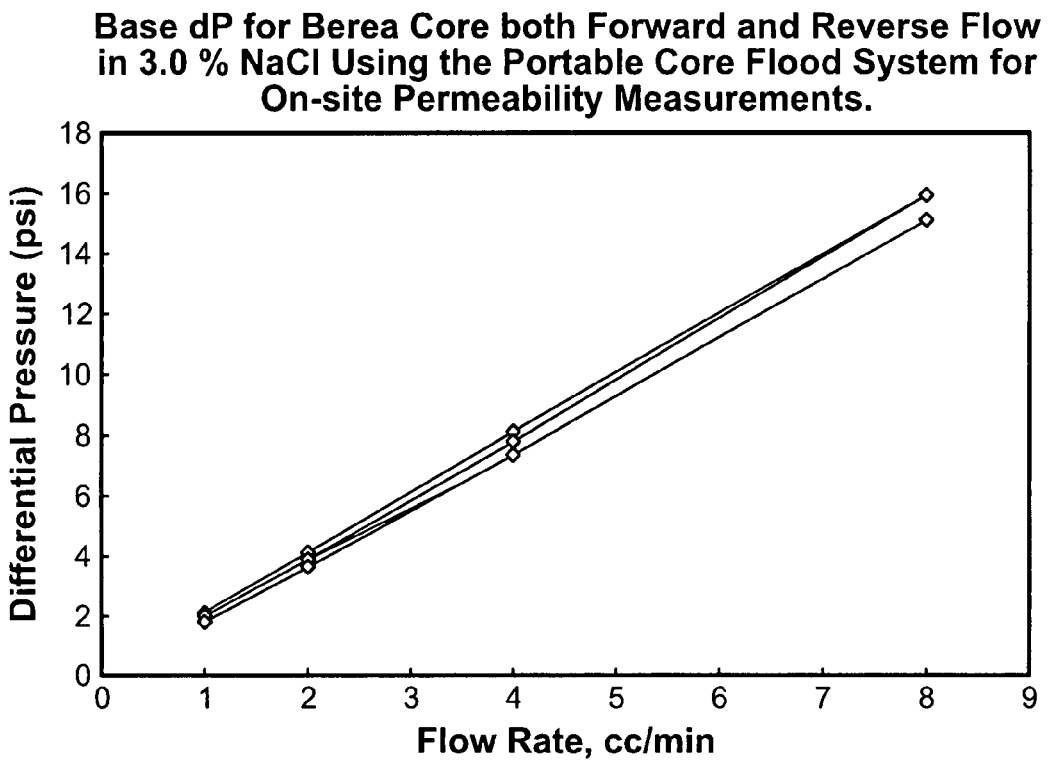

FIG. 14 is a replicated chart of example data readings for differential pressures obtained over a range of flow rates with an apparatus according to the present invention. FIG. 10 is a plot of those portions of the data from FIG. 14 for forward flow of the solution through the sample, and FIG. 11 is a plot of those portions of the data from FIG. 14 for reverse flow of the solution through the sample. FIG. 12 is a composite plot of the data displayed in FIGS. 10 and 11. The data of FIGS. 10 through 12 illustrate the linearity between measurements obtained of pressure differential as a function of flow rate.

From the foregoing, it can be seen that the permeability testing apparatus A of the present invention measures fluid permeabilities, such as water or oil, on-site of reservoir samples at ambient pressure or at reservoir pressure conditions. The on-site permeability testing apparatus A enables rapid measurement of the impact of injected brine or produced oil on reservoir core permeability in a minimal amount of time. The pressure regulators 80 and 186 assist in maintaining the pore flowing pressure without disturbing testing. Further, since the apparatus A is capable of use at the well site with freshly collected formation samples, the results are more accurate than those obtained in an off-site lab due to changes in the field water quality during transport times. The apparatus A of the present invention is thus capable of performing tests at field conditions rather than having to scale down or to simulate field conditions in a lab offsite from the well.

The apparatus A can monitor damage in reservoir core samples and also can sample fluids used either in the inlet or outlet lines without disturbing testing or pore pressure. The apparatus A can also be used for testing or monitoring quality of injected or disposed fluid into a reservoir. It can also assist in studying the impact of water quality on injectivity decline in wells or formations of interest.

The invention has been sufficiently described so that a person with average knowledge in the matter may reproduce and obtain the results mentioned in the invention herein. Nonetheless, any skilled person in the field of technique, subject of the invention herein, may carry out modifications not described in the request herein, to apply these modifications to a determined structure, or in the manufacturing process of the same, requires the claimed matter in the following Claims; such structures shall be covered within the scope of the invention.

It should be noted and understood that there can be improvements and modifications made of the present invention described in detail above without departing from the spirit or scope of the invention as set forth in the accompanying claims.

I claim:

1. An apparatus for permeability measurements of a core sample obtained from a subterranean reservoir, the apparatus comprising:
   a core sample holder receiving a core sample obtained from the subterranean reservoir for permeability testing;
   the core sample holder having first and second test ports at spaced locations from each other for receiving fluid for permeability testing of the core sample;
   a first accumulator containing a first fluid from the subterranean reservoir under a regulated pressure and flow rate for application to the core sample holder for permeability testing of the core sample;
   a second accumulator containing a second fluid from the subterranean reservoir under a regulated pressure and flow rate for application to the core sample holder for permeability testing of the core sample, the second fluid being a different fluid from the first fluid;

a pump providing calibrated fluid pressure and volume for core permeability testing;

a supply control valve connected to the first and second accumulators for selectively permitting passage of fluids from the first and second accumulators for application to the core sample holder;

a supply manifold connected between the control valve and the core sample holder for applying fluids received through the control valve to the core sample holder at selected controlled fluid pressure and flow rate to measure the permeability of the core sample to the applied fluid;

a first application control valve connected to the supply manifold for application of fluids from the supply manifold to the first test port of the core sample holder;

a first test fluid manifold connected between the first application control valve and the first test port of the core sample holder;

a second application control valve connected for application of fluids from the supply manifold to the second test port of the core sample holder;

a second test fluid manifold connected between the second application control valve and the first test fluid manifold;

a pressure regulator in fluid communication with the core sample holder for establishing an inlet pressure for the fluid applied to the sample holder;

a pressure transducer section for measuring pressure differential of the fluid between the test ports of the core sample holder, the pressure transducer section being connected to the supply manifold to sense fluid pressure in the supply manifold to obtain pressure readings regarding fluids in the accumulators, to the first test fluid manifold to obtain pressure readings at the first test port, and to the second test fluid manifold to obtain pressure readings at the second test port;

the pressure transducer section further comprising:

a first pressure differential transducer for measuring pressures in a first pressure range based on expected permeability of the core sample;

a second pressure differential transducer for measuring pressures in a second pressure range different from the first range based on expected permeability of the core sample;

a control valve selectively connecting the first pressure differential transducer and the second pressure differential transducer to the core sample holder based on expected permeability of the core sample; and a data processor for obtaining a measure of the relative permeability of the core sample based on the pressure differential measurements from the pressure transducer section and the fluid flow rates.

2. The apparatus of claim 1, wherein the pressure regulator includes a fluid sampler removing samples of the fluid while maintaining pore pressure in the core sample holder.

3. The apparatus of claim 1, further including an outlet pressure regulator in fluid communication with the core sample holder for establishing an outlet pressure for the core sample holder.

4. The apparatus of claim 3, wherein the outlet pressure regulator includes a fluid sampler removing samples of the fluid while maintaining pore pressure in the core sample holder.

5. The apparatus of claim 1, further comprising a filter used to separate solids and sediments from the pressurized fluids.

6. The portable core flood system of claim 1, further comprising a data display device for providing displays of data from the data processor.

7. The apparatus of claim 1, wherein the first fluid is brine from the subterranean reservoir.

8. The apparatus of claim 1, wherein the second fluid is produced oil from the subterranean reservoir.

9. The apparatus of claim 1, further comprising a heating element for application of heat to the core sample holder.

10. The apparatus of claim 9, wherein the heating element comprises heating tape.

11. The apparatus of claim 1, wherein the pressure transducer section further includes:

a bypass valve connected with the first pressure transducer allowing fluid pressure in the core sample holder to be sensed by the first pressure transducer; and a bypass valve connected with the second pressure transducer allowing fluid pressure in the core sample holder to be sensed by the second pressure transducer.

12. The apparatus of claim 1, further including:

a central outlet port formed in the core sample holder between the first and second fluid test ports; and a central outlet control valve operable independently of the first application control valve to connect the central outlet port to the pressure transducer section.

13. A modular apparatus transportable to a well site for permeability measurements of a core sample obtained from a subterranean reservoir of the well, the modular apparatus comprising:

a container module having a floor base, side walls and a partition between the side walls to form front and rear compartments;

a core sample holder mounted with the floor base of the module and receiving a core sample obtained from the subterranean reservoir for permeability testing;

the core sample holder having first and second test ports at spaced locations from each other for receiving fluid for permeability testing of the core sample;

a first accumulator mounted with a side wall of the module and containing a first fluid from the subterranean reservoir under a regulated pressure and flow rate for application to the core sample holder for permeability testing of the core sample;

a second accumulator mounted with the side wall of the module and containing a second fluid from the subterranean reservoir under a regulated pressure and flow rate for application to the core sample holder for permeability testing of the core sample, the second fluid being a different fluid from the first fluid;

a pump providing calibrated fluid pressure and volume for core permeability testing;

a supply control valve mounted with the side wall and connected to the first and second accumulators for selectively permitting passage of fluids from the first and second accumulators for application to the core sample holder;

a supply manifold mounted with the floor of the module and connected between the control valve and the core sample holder for applying fluid received through the control valve to the core sample holder at selected controlled fluid pressure and flow rate to measure the permeability of the core sample to the applied fluid;

a first application control valve connected to the supply manifold for application of fluids from the supply manifold to the first test port of the core sample holder;

a first test fluid manifold connected between the first application control valve and the first test port of the core sample holder;

a second application control valve connected for application of fluids from the supply manifold to the second test port of the core sample holder;

a second test fluid manifold connected between the second application control valve and the first test fluid manifold;

a pressure regulator in fluid communication with the core sample holder for establishing an inlet pressure for the fluid applied to the core sample holder;

a pressure transducer section mounted with the partition of the module for measuring pressure differential of the fluid between the test ports of the core sample holder, the pressure transducer section being connected to the supply manifold to sense fluid pressure in the supply manifold to obtain pressure readings regarding fluids in the accumulators, to the first test fluid manifold to obtain pressure readings at the first test port, and to the second test fluid manifold to obtain pressure readings at the second test port;

the pressure transducer section further comprising:

a first pressure differential transducer for measuring pressures in a first pressure range based on expected permeability of the core sample;

a second pressure differential transducer for measuring pressures in a second pressure range different from the first range based on expected permeability of the core sample;

a control valve selectively connecting the first pressure differential transducer and the second pressure differential transducer to the core sample holder based on expected permeability of the core sample; and a data processor mounted on an upper portion of the module for obtaining a measure of the relative permeability of the core sample based on the pressure differential measurements and the fluid flow rates.

* * * * *